United States Patent [19]

Celmer et al.

[11] 4,001,397

[45] Jan. 4, 1977

[54] ANTIBIOTIC COMPOUND 41,012

[75] Inventors: Walter D. Celmer, New London; Charles E. Moppett, Mystic; Walter P. Cullen, East Lyme; John B. Routien, Lyme; Mark T. Jefferson, Waterford, all of Conn.; Riichiro Shibakawa, Handa; Junsuke Tone, Chita, both of Japan

[73] Assignee: Pfizer Inc., New York, N.Y.

[22] Filed: Aug. 11, 1975

[21] Appl. No.: 603,366

[52] U.S. Cl. .............................. 424/116; 195/80 R
[51] Int. Cl.² ....................................... A61K 35/74
[58] Field of Search .................. 424/116; 195/80 R

[56] References Cited

UNITED STATES PATENTS

| 3,143,467 | 8/1964 | Hamill et al. | 424/116 |
| 3,272,709 | 9/1966 | Bergy et al. | 424/116 |
| 3,697,648 | 10/1972 | Shomuva et al. | 424/116 |

Primary Examiner—Jerome D. Goldberg
Attorney, Agent, or Firm—Connolly and Hutz

[57] ABSTRACT

Disclosed is a new antibiotic, Compound 41,012, which is produced by the submerged aerobic fermentation of a new species of Actinoplanes designated *Actinoplanes nipponensis* sp. nov. Routien, ATCC 31145. Methods for the recovery and purification of Compound 41,012 are also described as are some of its antimicrobial properties.

2 Claims, 1 Drawing Figure

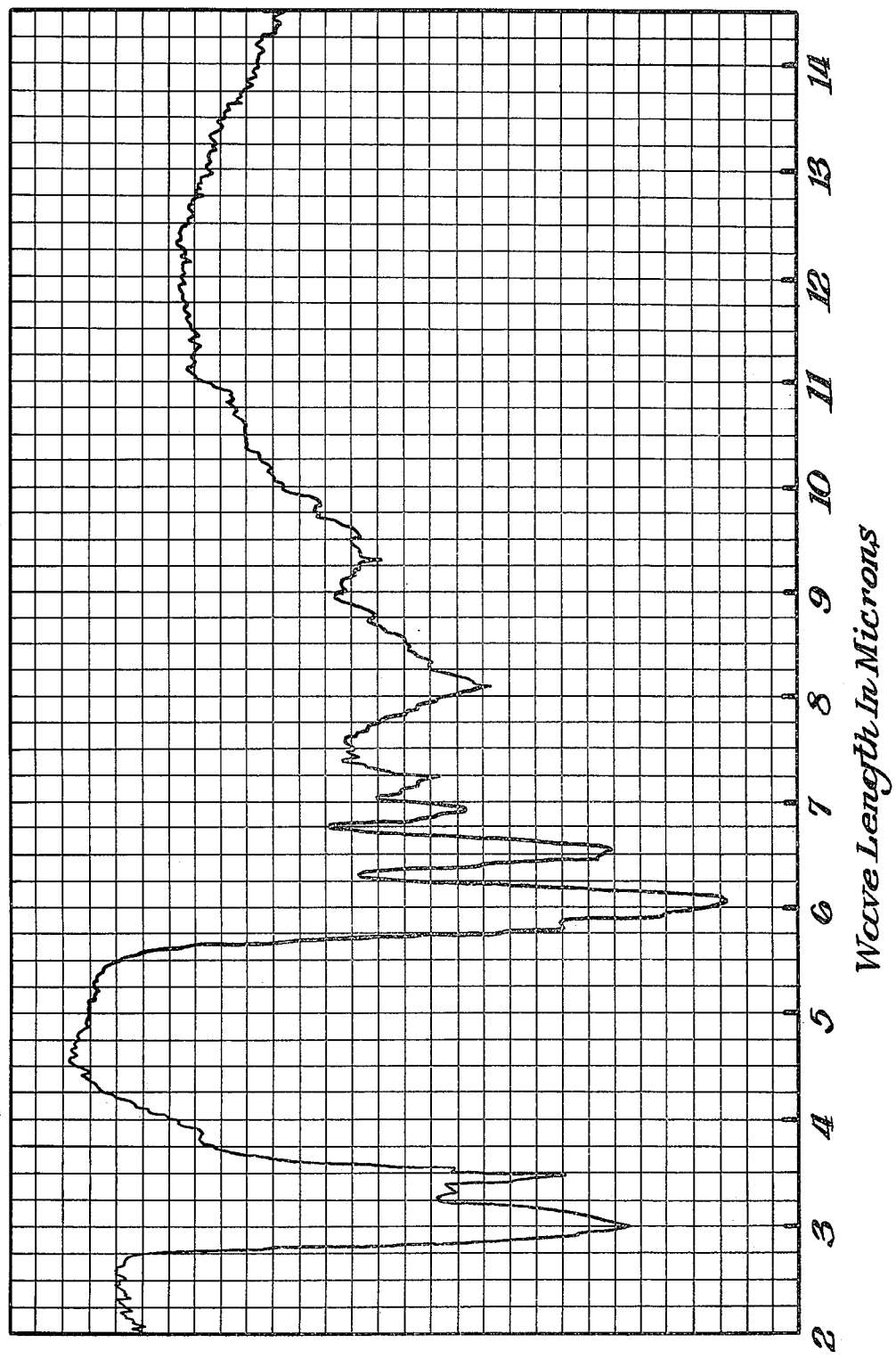

ANTIBIOTIC COMPOUND 41,012

BACKGROUND OF THE INVENTION

The literature describes a series of closely related acidic polypeptide antibiotics containing the same amino acids in identical ratios and apparently in the same sequence but differing in respect to their individual fatty acid constituents. These antibiotics are active against Gram-positive bacteria with little or no activity against Gram-negative bacterial, yeasts or fungi.

This group of closely related acidic polypeptide antibiotics includes the following illustrative members: amphomycin, Antibiot. Chemother., 3, 1239 (1953); glumamycin, J. Antibiotics, Ser. A, 15, 1 (1962); zaomycin, J. Antibiotics, Ser. A, 7, 134 (1954); aspartocin, Antibiot. Ann., 194 (1960); and tsushimycin, J. Antibiotics, 21, 439 (1968).

SUMMARY OF THE INVENTION

This invention is concerned with Compound 41,012, a new acidic polypeptide antibiotic produced under submerged aerobic fermentation conditions by *Antinoplanes nipponensis* sp. nov. Routien, ATCC 31145.

DETAILED DESCRIPTION OF THE INVENTION

The microorganism useful for the preparation of the antibiotic of this invention was isolated from a soil sample from Japan. This culture (Pfizer F.D. 24834), designated *Actinoplanes nipponensis* sp. nov. Routien, has been deposited in The American Type Culture Collection, Rockville, Md. under their accession number ATCC 31145. The permanency of the deposit and ready accessibility thereto by the public are afforded in the event the patent is granted. Access to the culture is avilable during pendency of the application under Rule 14 and 35 USC 112. All restrictions on the availability to the public of the culture deposited will be irrevocably removed upon granting of the patent.

The initial examination showed the culture to have no aerial hyphae but, instead, sporangia typical of the genus Actinoplanes. It was, therefore, planted on various media typically used by various investigators of this genus. Incubation was at 28° C. except where otherwise noted. The results were recorded at various times up to five weeks, the time dependent on the medium and the customary period of incubation.

The media and references are as follows:
1. Czapek's Solution Agar. Waksman, S. A. *The Actinomycetes II*, medium no. 1, pg. 328, 1961.
2. Peptone Czapek — Solution Agar. Made as No. 1 with the addition of 1% peptone.
3. Aino Henssen Agar. A. Henssen. *Archiv fur Mikrobiologie* Bd. 26 S. 373–414. 1957. First medium in Table 1.
4. Glucose-Asparagine Agar. Waksman, *The Actinomycetes* II, Medium no. 2, pg. 328, 1961.
5. Bennett's Agar. Ibid. Medium No. 30, pg. 331.
6. Tyrosine Agar. Shirling, E. B. and D. Gottlieb. *Internat. Jr. Systematic Bacteriology* 16:313–340. 1966. ISP Medium No. 7.
7. Oatmeal Agar. Ibid. ISP Medium No. 3.
8. Glycerol-Asparagine Agar. Ibid. ISP Medium No. 5.
9. Calcium Malate Agar. Waksman. Bact. Rev. 21:1–29. 1957.
10. Yeast extract — malt extract agar. Shirling and Gottlieb. *Internat. Jr. Sys. Bact.* 16:313–340. 1966. ISP medium No. 2.
11. Tryptone-yeast extract broth. Ibid. ISP Medium No. 1.
12. Gelatin. Gordon, R. E. and J. M. Mihm. *Jr. Bact.* 73:15–27. 1957.
13. Starch (Inorganic Salts Starch Agar). Shirling and Gottlieb. *Internat. Jr. Sys. Bact.* 16:313–340. 1966. ISP Medium No. 4.
14. Peptone-yeast extract iron agar (plus lead acetate strips). Ibid. ISP Medium No. 6.
15. Skim Milk.
16. Dextrose Nitrate Broth. Waksman. *The Actinomycetes* II, Medium No. 1, pg. 328, (1961).
17. Organic Nitrate Broth. Gordon and Mihm. *Jr. Bact.* 73:15–27. 1957.
18. Carbohydrate Utilization Media. Shirling and Gottlieb. *Internat. Jr. Sys. Bact.* 16:313–340. 1966. ISP Medium No. 9.
19. Potato Carrot Agar. Lechevalier, M.P., *Jr. Lab. and Clinical Med.* 71:934–944. 1968 but made with 30 g. potatoes, 2.5 g carrots and 20 g agar.

The results of the investigation, with the time of observation indicated where appropriate, are as follows (colors with capitalized names are those of Ridgway, *Color Standards and Nomenclature* 1912):

Glucose Asparagine Agar (14 days): growth moderate, flat, Apricot Buff; reverse Apricot Buff; no soluble pigment.

Bennett's Agar (14 days): growth good, raised and wrinkled, Salmon Orange to Cinnamon Rufous in center of streak; reverse near Cinnamon Rufous; soluble pigment pale brown.

Oatmeal Agar (14 days): growth moderate, flat, Salmon Buff; reverse Salmon Buff; no soluble pigment.

Glycerol Asparagine Agar (14 days): growth very poor, thin, flat, Salmon Buff to Apricot Buff; reverse Salmon Buff; no soluble pigment.

Peptone — Yeast Extract Agar (14 days): growth moderate in isolated colonies, raised and wrinkled, Apricot Orange; reverse Apricot Orange; no soluble pigment.

Calcium Malate Agar (14 days): growth barely visible, thin, flat, Sea Shell Pink; reverse not visible; no soluble pigment.

Gelatin (14 days): growth poor, thin, flat, Cinnamon Rufous; reverse Cinnamon Rufous; no soluble pigment.

Starch Agar (14 days): growth moderate, slightly roughened, Apricot Buff; reverse Apricot Buff; no soluble pigment.

Tyrosine Agar (14 days): growth moderate to good, raised, Cinnamon Rufous; reverse Cinnamon Rufous; pale lavendar pink soluble pigment.

Czapek Solution Agar (5 weeks): growth moderate (point planting 1 cm. wide), rather flat, bright orange; reverse bright orange; no soluble pigment.

Peptone-Czapek Solution Agar (5 weeks): growth moderate (point planting 1 cm. wide), flat, pale yellowish-orange in center, light orange in outer part; reverse pale orange; no soluble pigment.

Aino Hensson Agar (5 weeks): growth moderate (point planting 1 cm. wide), flat, edge irregular, bright reddish-orange; reverse bright reddish-orange; no soluble pigment.

Biochemical Properties: starch with narrow (3 mm.) zone of hydrolysis in 7 days; gelatin with 9 mm. liquified zone in 7 days; no melanin in 7 days; $H_2S$ produced in 7 days; nitrate reduced to nitrite in both dextrose nitrate broth and organic nitrate broth in 7 days; calcium malate not digested in 14 days; tyrosine not digested in 14 days; milk with orange ring but no change in 7 days but in 15 days showing coagulation and partial peptonization in two of six tubes.

Carbohydrate Utilization: Utilization pattern (scored as in ISP directions by Shirling and Gottlieb, *Internat. Jr. Sys. Bact.* 16:313–340. 1966) after 14 days.

| Compound | Growth |
| --- | --- |
| No carbon | Trace |
| Glucose | Positive |
| Arabinose | ++ |
| Fructose | ++ |
| Inositol | + |
| Mannitol | ± |
| Raffinose | + |
| Rhamnose | + |
| Sucrose | ++ |
| Xylose | ++ |

Sporangia: found on potato-carrot agar and on mannitol agar. Description from mannitol agar: irregular in shape, 5.5–12 μm wide, in a loose palisade layer. Spores round, 1–1.5 μm wide to oval, 1.5–1.0 μm, non-motile in water after 30 min. or in a solution of 0.1% glucose plus 0.1% Tween 80 after 15 minutes.

Based on the above observations, this organism did not appear to fit the description of any of the species of Actinoplanes described in *Bergey's Manual of Determinative Bacteriology*, 8th edition, 1974, though it came closest to *A. utahensis*. However, it did not agree with the description of this species as given in *Bergey's Manual*, nor with the strain identified as *A. utahensis* in U.S. Pat. No. 3,824,305, nor with a description of the type culture of this species based on study of it in our laboratory. The culture also did not appear to fit any species described in any other patent or in various journals dealing with such organisms, and thus it was determined to be a new species and was designated *Actinoplanes nipponensis* sp. nov. Routien. It was deposited in the American Type Culture Collection as ATCC 31145.

Cultivation of this species of *A. nipponensis* preferably takes place in aqueous nutrient media under aerobic, submerged conditions with agitation. Appropriate temperatures for cultivation range from about 28° to 36° C. Nutrient media which are useful for fermentation production of Compound 41,012 include a source of assimilable carbon such as sugars, starch, glycerol and molasses, a source of organic nitrogen such as fish meal, casein, enzymatic digest of casein, meat meal, wheat gluten, cottonseed meal soybean meal and peanut meal. A source of growth substances such as distillers' solubles and/or yeast extract as well as salts such as sodium chloride, ammonium acetate, ammonium sulfate, potassium phosphate and trace minerals such as iron, manganese, magnesium, zinc and cobalt may also be utilized with advantageous results. If excessive foaming is encountered during fermentation, antifoam agents such as vegetable oils or silicones may be added to the fermentation medium. The pH of the fermentation tends to remain rather constant but if variations are encountered, a buffering agent such as calcium carbonate may also be added to the medium. Aeration of the medium in tanks for submerged growth is preferably maintained at the rate of about ½ to 2 volumes of free air per volume of broth per minute. Agitation may be maintained by means of agitators generally familiar to those in the fermentation industry. Aseptic conditions must, of course, be maintained through the transfer of the microorganism and throughout its growth.

Inoculum for the preparation of the antibiotic may be obtained by employing growth from slants or Roux bottles of *A. nipponensis* ATCC 31145. The growth may be used to inoculate either shake flasks or inoculum tanks, or alternatively, the inoculum tanks may be seeded from the shake flasks. The growth of the microorganism usually reached its maximum in about two or three days. However, variations in the equipment used, aeration, rate of stirring, etc. may affect the speed with which the maximum growth is reached. In general, the fermentation is conducted until substantial antimicrobial activity is imparted to the medium, a period of from about 24 hours to about 4 days being sufficient for most purposes.

The process of antibiotic production is conveniently followed during fermentation by biological assay of the broth employing *Bacillus subtilis*. All samples are bioassayed at pH 7.0–8.5 because the zones of inhibition are markedly diminished at acid pH, in particular pH 4.0.

Compound 41,012 may be recovered from fermentation broth by a number of different procedures including solvent extraction, preferably with n-butanol, and adsorption on Amberlite XAD-2 (Rohm and Haas, Philadelphia, Pa.).

The preferred method of separation and recovery of Compound 41,012 is as follows: Filtered fermentation broth is stirred with Amberlite XAD-2 at room temperature for about an hour or, alternatively, the filtered broth is contacted with the resin contained in a packed column. The adsorbed antibiotic is removed from the resin by elution with methanol. Evaporation of the methanol in vacuo is followed by the addition of n-propanol with its subsequent removal in vacuo. The slurry is treated with either acetone or heptane to give solid material which is collected by filtration.

Thin layer chromatography employing silica gel is a useful tool for analyzing the antibiotic produced by *A. nipponensis* ATCC 31145 in fermentation media and the composition of crude and purified materials separated from fermentation broths. The developing system may be n-propanol:2 N ammonium hydroxide (80:25—v/v), n-butanol:acetic acid:water (4:1:1 — v/v/v) or, preferably, chloroform: ethanol:water (4:7:2 — v/v/v). Compound 41,012 may be visualized by spraying air-dried developed plates with water. The antibiotic shows up as a white spot on a dull grey background. Bioautographic detection of the antibiotic may be accomplished by means of an overlay of a thin layer of nutrient agar seeded with a sensitive stream of *Staphylococcus aureus* or *Bacillus subtilis*.

The solids recovered through the use of Amberlite XAD-2 are purified by chromatography on silica gel 60 (E. Merck, Darmstadt, Germany) eluting with chloroform:ethanol:water (4:7:1 to 4:7:2 — v/v/v). The material obtained in this fashion is dissolved in water saturated with n-butanol and washed with an equal volume of pH 8.9 phosphate buffer followed by pH 3.0 phosphate buffer. The n-butanol layer is then washed with 2% aqueous sodium chloride solution, dried over sodium sulfate, treated with activated charcoal (Darco G60), filtered and evaporated in vacuo to give the free acid form of antibiotic Compound 41,012 as a white, amorphous material. If desired, the ammonium, potassium, sodium, calcium and other pharmaceutically-acceptable metal salts may be prepared by treatment of a solution of antibiotic acid with the appropriate base.

If the material recovered from the filtered broth is of low antibiotic potency, it may be partially purified by counter-current distribution with the system n-butanol:methylisobutyl ketone: pH 8.8 phosphate buffer (disodium hydrogen phosphate 50 grams per liter) — 2:3:5, v/v/v prior to chromatography on silica gel 60. The desired antibiotic Compound 41,012 is found primarily in the aqueous phase of plate 0 from which it may be extracted with n-butanol.

The present invention includes within its scope the dilute forms and crude concentrates separated from the fermentation broth as well as the purified antibiotic. All of these products are useful in combatting microorganisms, especially *Mycobacterium tuberculosis*, *Diplococcus pneumoniae*, *Streptococcus pyrogenes* and *Staphylococcus aureus*. In addition they are useful as disinfectants against such mircoogranisms and as an aid in the purification of mixed cultures for medical and diagnostic and biological research purposes.

Table I illustrates the antibiotic spectrum of Compound 41,012. These tests were run by preparing tubes of nutrient broth with gradually increasing concentrations of the pure antibiotic and then seeding the broths with the particular organism specified. The minimal inhibitory concentration indicated in Table I is the minimal concentration of the antibiotic in micrograms per ml at which the microorganisms failed to grow. The tests were conducted under standardized conditions as described in Proc. Soc. Exp. Biol. & Med., 122, 1107 (1966). Mice experimentally infected with *Staphylococcus aureus* are protected by subcutaneous administration of Compound 41,012 at about 25–50 mg/kg.

Table I

| Organism | Compound 41,012 |
| --- | --- |
| *Staph. aureus* | |
| 01A005 | 6.25 |
| 01A052 | 6.25 |
| 01A109 | 6.25 |
| 01A110 | 3.12 |
| 01A111 | 6.25 |
| 01A087 | 6.25 |
| 01A400 | 6.25 |
| *Strep. faecalis* | |
| 02A006 | 6.25 |
| *Mycobact. smegmatis* | |
| 05A001 | 12.50 |
| *B. subtilis* | |
| 06A001 | 0.78 |
| *E. coli* | |
| 51A229 | >200 |
| 51A266 | >200 |
| 51A125 | >200 |
| *Ps. aeruginosa* | |
| 52A104 | >200 |
| 52A440 | >200 |
| *Klebsiella pneumoniae* | |
| 53A009 | >200 |
| 53A031 | >200 |
| *Proteus mirabilis* | |
| 57C064 | >200 |
| *Proteus morgani* | |
| 57G001 | >200 |
| *Salm. cholerae-suis* | |
| 58B242 | >200 |
| *Salm. typhimurium* | |
| 58D009 | >200 |
| 58D013-C | >200 |

Solutions or suspensions of the antibiotic in a pharmaceutically-acceptable carrier such as water, peanut oil or propylene glycol can be administered via the parenteral route for the treatment in animals, including humans, of pneumococcal, streptococcal, tubercular and other antibiotic-sensitive infections. In general, the antibiotic is desirably administered by parenteral injections of 100 to 500 mg, depending on the type and severity of the infection and weight of the subject being treated.

For topical applications, aqueous or ethanolic solutions or cream or ointment formulations of the antibiotic (0.5–2.0% w/v) may be employed.

EXAMPLE I

A sterile aqueous medium having the following composition was prepared:

| Ingredient | Grams/liter |
| --- | --- |
| Glucose | 10 |
| Starch | 20 |
| Yeast extract | 5 |
| Enzymatic digest of casein | 5 |
| Meat meal | 5 |
| $K_2HPO_4$ | 0.5 |
| $CoCl_2 . 6H_2O$ | 0.002 |
| $CaCO_3$ | 4 |
| pH - 7.1–7.2 | |

Cells from a slant culture of *A. nipponensis* ATCC 31145 were transferred to each of a number of 300 ml shake flasks containing 50 ml of this medium and shaken on a rotary shaker for about three to four days at 28° C.

Fermentors containing two liters of the following sterile medium were seeded with 5% v/v of the grown inoculum.

| Ingredient | Grams/liter |
| --- | --- |
| Glucose | 30 |
| Soy flour | 20 |
| $Fe_2(SO_4)_3$ | 0.3 |
| $MnCl_2 . 4H_2O$ | 0.3 |
| $CoCl_2 . 6H_2O$ | 0.002 |
| pH - 7.1 | |

The temperature was maintained at 28° to 36° C. and the fermentor stirred at 1700 r.p.m. and aerated at the rate of about one volume of air per volume of broth per minute.

After about 60 to 90 hours, the broth is filtered and extracted twice with ⅓ to ½ volumes of n-butanol. The separated solvent extract was concentrated in vacuo and the antibiotic precipitated by the addition of heptane.

EXAMPLE II

The fermentation process of Example I was repeated. The filtered broth (18 liters) was stirred at room temperature for an hour with 1.4 liters of Amberlite XAD-2. The resin suspension was poured into a 2 inch diameter column and the packed resin washed with 4 gallons of water. Alternatively, the filtered fermentation broth may be passed over the packed resin in the 2 inch diameter column three times with a subsequent water wash.

Compound 41,012 was removed from the resin by elution with 7 liters of methanol. Evaporation of the methanol in vacuo was followed by the addition of n-propanol with its removal in vacuo. The resultant slurry was then treated with acetone or heptane to give solid material which was collected by filtration. The solids were dried in vacuo to constant weight 22 grams.

The solids (10 grams) were purified by chromatography on silica gel 60 contained in a 1 inch × 92 cm column and eluting with chloroform:ethanol:water (4:7:1 to 4:7:2 — v/v/v). The appropriate fractions were pooled and evaporated in vacuo to dryness (4 grams). The material was dissolved in 200 ml of water saturated n-butanol and washed with an equal volume of pH 8.9 phosphate buffer followed by pH 3.0 phosphate buffer. The n-butanol layer was then washed with 200 ml of 2% aqueous sodium chloride solution, dried over sodium sulfate, treated with 4 grams activated charcoal (Darco G60), filtered and evaporated in vacuo to give 1.35 grams of the free acid form of antibiotic Compound 41,012 as a white, amorphous material. This material is soluble in water, methanol, ethanol, water saturated n-butanol, dimethylformamide and dimethylsulfoxide; it is insoluble in heptane, diethyl ether, chloroform and methylene chloride.

Antibiotic Compound 41,012, dried in vacuo at 70° over phosphorus pentoxide for about 36 hours gives on analysis the following average proportions:

Carbon 44.81
Hydrogen 6.56
Nitrogen 9.55
Oxygen (by difference) 39.08

Compound 41,012 is optically active, having a rotation of $[\alpha]_D^{25°} = -7.1°$ ($c = 1$, MeOH). There is no absorption in the ultraviolet region.

The infrared spectrum of Antibiotic Compound 41,012 is attached. When pelleted in KBr, characteristic absorption in the infrared region occur at the following wavelengths in microns: 3.00, 3.48, 5.80, 5.93, 6.07, 6.55, 6.92, 7.25 and 8.10.

What is claimed is:

1. The Antibiotic Compound 41,012 which in the form of the free acid is soluble in water, ethanol, water saturated n-butanol, dimethylformamide or dimethylsulfoxide and insoluble in heptane, diethyl ether, chloroform or methylene chloride; has an optical rotation of $[\alpha]_D^{25°} = -7.1°$ at a concentration of 1% in methanol; has an average composition by weight of 44.81% carbon, 6.56% hydrogen, 9.55% nitrogen and 39.08% oxygen (by difference); and when pelleted in KBr exhibits characteristic absorption in the infrared region at the following wavelengths in microns: 3.00, 3.48, 5.80, 5.93, 6.07, 6.55, 6.92, 7.25 and 8.10.

2. A process for producing Antibiotic Compound 41,012 as defined in claim 1 which comprises cultivating *Actinoplanes nipponensis* sp. nov. Routien ATCC 31145 at a temperature of 28°–36° C. in an aqueous nutrient medium containing a source of carbohydrate, a source of assimilable nitrogen and inorganic salts under submerged aerobic conditions until substantial antimicrobial activity is imparted to said medium.

* * * * *